United States Patent
Jia et al.

(10) Patent No.: US 7,700,667 B2
(45) Date of Patent: Apr. 20, 2010

(54) DENTAL RESIN COMPOSITION, METHOD OF MANUFACTURE, AND METHOD OF USE THEREOF

(75) Inventors: Weitao Jia, Wallingford, CT (US); Shuhua Jin, Wallingford, CT (US)

(73) Assignee: Pentron Clinical Technologies, LLC, Wallingford, CT (US)

( * ) Notice: Subject to any disclaimer, the term of this patent is extended or adjusted under 35 U.S.C. 154(b) by 858 days.

(21) Appl. No.: 11/046,093

(22) Filed: Jan. 28, 2005

(65) Prior Publication Data

US 2005/0192374 A1  Sep. 1, 2005

Related U.S. Application Data

(60) Provisional application No. 60/540,148, filed on Jan. 29, 2004.

(51) Int. Cl.
    - A61K 6/08  (2006.01)
    - A61K 6/02  (2006.01)
    - A61K 6/083 (2006.01)
    - A61C 5/09  (2006.01)
    - C09K 3/00  (2006.01)

(52) U.S. Cl. .............. 523/115; 523/116; 523/118; 433/228.1; 106/35

(58) Field of Classification Search .......... 523/109, 523/115, 116, 118; 433/228.1
    See application file for complete search history.

(56) References Cited

U.S. PATENT DOCUMENTS

| | | |
|---|---|---|
| 3,066,112 A | 11/1962 | Bowen |
| 3,194,784 A | 7/1965 | Bowen |
| 3,926,906 A | 12/1975 | Lee, II et al. |
| 4,148,988 A | 4/1979 | Masuhara et al. |
| 4,504,635 A * | 3/1985 | Weber et al. ............ 525/450 |
| 4,544,359 A | 10/1985 | Waknine |
| 4,547,531 A | 10/1985 | Waknine |
| 4,659,751 A | 4/1987 | Bowen |
| 4,691,045 A * | 9/1987 | Fukuchi et al. .......... 560/185 |
| 4,732,943 A | 3/1988 | Beech et al. |
| 4,786,749 A * | 11/1988 | Koleske et al. .......... 560/76 |
| 4,883,899 A * | 11/1989 | Muramoto et al. ........ 560/14 |
| 5,171,763 A * | 12/1992 | Ohno et al. ............. 523/116 |
| 5,260,476 A * | 11/1993 | Ohno et al. ............. 560/90 |
| 5,264,513 A * | 11/1993 | Ikemura et al. ......... 526/318 |
| 5,276,068 A | 1/1994 | Waknine |
| 5,348,988 A | 9/1994 | Suh et al. |
| 5,525,648 A | 6/1996 | Aasen et al. |
| 5,756,560 A | 5/1998 | Antonucci et al. |
| 5,925,690 A * | 7/1999 | Fuchigami et al. ....... 523/118 |
| 5,969,000 A | 10/1999 | Yang et al. |
| 6,013,694 A | 1/2000 | Jia et al. |
| 6,071,983 A | 6/2000 | Yamamoto et al. |
| 6,147,137 A | 11/2000 | Jia |
| 6,217,644 B1 | 4/2001 | Matsunae et al. |
| 6,291,548 B1 | 9/2001 | Akahane et al. |
| 6,326,417 B1 * | 12/2001 | Jia ........................ 523/116 |
| 6,649,669 B2 * | 11/2003 | Dickens .................. 522/76 |
| 6,653,365 B2 | 11/2003 | Jia |
| 6,673,958 B2 | 1/2004 | Tiba et al. |
| 6,759,449 B2 | 7/2004 | Kimura et al. |
| 6,815,470 B2 | 11/2004 | Ibaragi et al. |
| 6,939,900 B2 | 9/2005 | Ario et al. |

(Continued)

OTHER PUBLICATIONS

S. Venz and B. Dickens: Modified Surface-Active Monomers for Adhesive Bonding to Dentin; J Dent Res 72(3):582-586, Mar. 1993: PMGDM resin.

*Primary Examiner*—Mark Eashoo
*Assistant Examiner*—Michael Pepitone
(74) *Attorney, Agent, or Firm*—Cantor Colburn LLP

(57) ABSTRACT

A composition is disclosed comprising a polymerizable (meth)acrylate of the structure:

$$\left( \overset{O}{\underset{\|}{C}} O[CR^1R^2]_x - M - [CR^3R^4]_y O \overset{O}{\underset{\|}{C}} C \overset{R^5}{=} CH_2 \right)_m$$

$$A_a \left[ \begin{array}{c} \\ \end{array} \right] (COOH)_n$$

$$\left( \overset{\|}{\underset{O}{C}} OW[O \overset{\|}{\underset{O}{C}} C = CH_2]_z \right)_q$$
$$\phantom{xxxxxxxxxx} R^5$$

wherein A is an anhydride; a is 0 or 1; n is 0, 1, 2, or 3; $R^1$, $R^2$, $R^3$, and $R^4$ are each independently hydrogen, hydroxy, $C_1$-$C_{12}$ alkyl, $C_1$-$C_{12}$ perhaloalkyl, $C_1$-$C_{12}$ alkoxy, $C_1$-$C_{12}$ perhaloalkoxy, $C_2$-$C_{12}$ alkenyl, $C_2$-$C_{12}$ alkynyl, ($C_1$-$C_6$ alkyl)-O-($C_1$-$C_6$ alkylene), or hydroxy($C_1$-$C_6$ alkylene); x and y are each independently an integer of 1 to 10; z is an integer of 1 to 5; $R^5$ is hydrogen or methyl; M is $$-\overset{O}{\underset{\|}{C}}-, \quad -\overset{O}{\underset{\|}{C}}-G-,$$

$$-G-\overset{O}{\underset{\|}{C}}-, \quad \text{or} \quad -G-\overset{O}{\underset{\|}{C}}-J-$$

wherein G and J are each independently O or $NR^6$, wherein $R^6$ is hydrogen or $C_1$-$C_6$ alkyl; m is 1, 2, 3, or 4; W is an organic group having the valency of z+1; and q is 0 or 1; and further wherein when a is 1, n+m+q is 1, 2, 3, or 4, and when a is 0, n+m+q is 1, 2, 3, 4, 5, or 6. The composition finds use as a dental resin.

13 Claims, 1 Drawing Sheet

U.S. PATENT DOCUMENTS

| | | |
|---|---|---|
| 2002/0045678 A1* | 4/2002 | Lopez et al. ............... 523/116 |
| 2002/0082317 A1 | 6/2002 | Lyons et al. |
| 2002/0120033 A1* | 8/2002 | Jia et al. ................... 523/115 |
| 2003/0055124 A1 | 3/2003 | Klee et al. |
| 2003/0125444 A1 | 7/2003 | Jia et al. |
| 2003/0175659 A1 | 9/2003 | Tiba et al. |
| 2003/0207960 A1* | 11/2003 | Jia ............................ 523/115 |
| 2004/0054027 A1 | 3/2004 | Lyons et al. |
| 2004/0156795 A1 | 8/2004 | Nemoto et al. |
| 2004/0229973 A1 | 11/2004 | Sang et al. |
| 2004/0235981 A1 | 11/2004 | Qian |
| 2005/0014861 A1 | 1/2005 | Qian |
| 2005/0020720 A1 | 1/2005 | Dickens et al. |
| 2005/0038135 A1 | 2/2005 | Jin et al. |
| 2005/0049326 A1 | 3/2005 | Park et al. |
| 2005/0277706 A1 | 12/2005 | Han et al. |
| 2007/0197682 A1* | 8/2007 | Jia et al. ................... 523/116 |
| 2007/0197683 A1* | 8/2007 | Jia et al. ................... 523/116 |
| 2007/0299157 A1 | 12/2007 | Sang et al. |
| 2008/0242761 A1 | 10/2008 | Jia et al. |

* cited by examiner

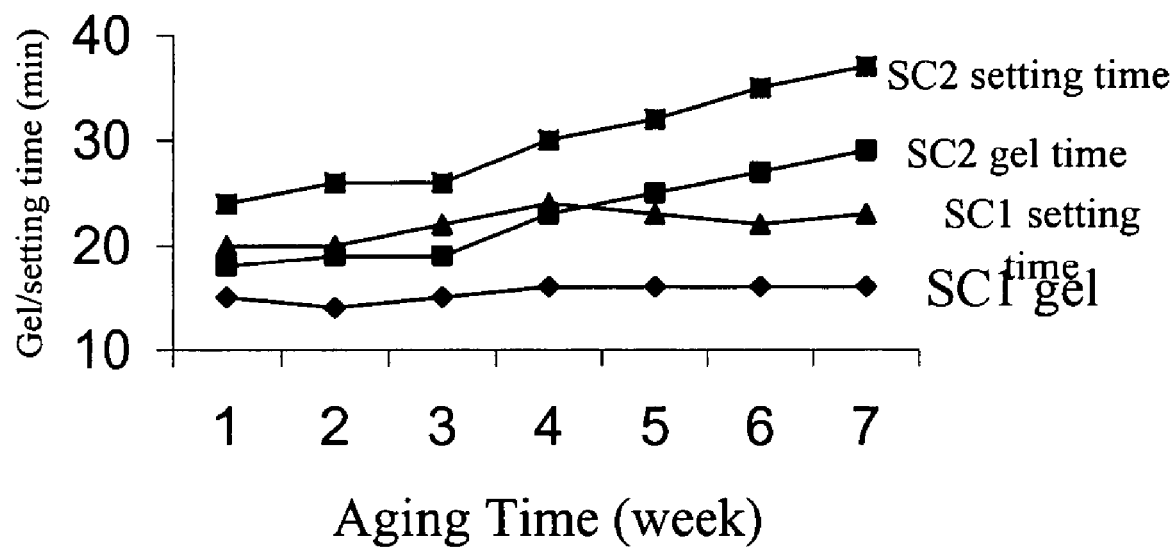

DENTAL RESIN COMPOSITION, METHOD OF MANUFACTURE, AND METHOD OF USE THEREOF

CROSS-REFERENCE TO RELATED APPLICATIONS

This application claims the benefit of U.S. Provisional Patent Application Ser. No. 60/540,148 filed Jan. 29, 2004.

BACKGROUND

This invention relates to dental resin compositions comprising polymerizable (meth)acrylate resins, their method of manufacture, and the use of such resins for restorative dentistry, including dental adhesives, dental cements, dental filling materials, root canal sealants, crown and bridge materials, and the like.

In recent years, materials used for dental restorations have principally comprised acrylate or methacrylate resins. Resinous materials of this type are disclosed, for example, in U.S. Pat. No. 3,066,112 to Bowen, No. 3,194,784 to Bowen, and No. 3,926,906 to Lee et al. An especially important methacrylate monomer is the condensation product of bisphenol A and glycidyl methacrylate, 2,2'-bis[4-(3-methacryloxy-2-hydroxy propoxy)-phenyl]-propane ("BisGMA"). Alternatively, BisGMA may be synthesized from the diglycidyl ether of bisphenol A and methacrylic acid (see, e.g., U.S. Pat. No. 3,066,112 to Bowen).

Because the wear and abrasion characteristics and the overall physical, mechanical, and optical properties of these unfilled acrylic resinous materials is poor, and because acrylic resin systems exhibit high coefficients of thermal expansion relative to the coefficient of thermal expansion of the tooth structure, these substances by themselves are less than satisfactory. In particular, the disparity in thermal expansion coupled with high shrinkage upon polymerization results in poor marginal adaptability, and ultimately leads to secondary decay. Composite dental restorative materials containing acrylate or methacrylate resins and fillers were thus developed. The fillers are generally inorganic materials based on silica, silicate based glasses, or quartz. These filled compositions are useful for a variety of dental treatments and restorative functions including crown and bridge materials, fillings, adhesives, sealants, luting agents or cements, denture base materials, orthodontic materials and sealants, and other dental restorative materials. Despite their suitability for their intended purposes, however, many of these materials have shrinkages of about two to about four percent by volume upon polymerization.

There accordingly remains a need in the art for dental resin materials that have good bonding adhesion to a dental substrate and minimal shrinkage upon polymerization without sacrificing other advantageous physical properties.

SUMMARY

The above-described need is met by a composition comprising a polymerizable (meth)acrylate of general structure I:

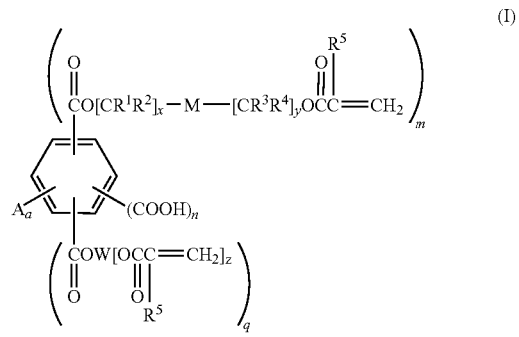

wherein
A is an anhydride;
a is 0 or 1;
n is 0, 1, 2, or 3;
$R^1$, $R^2$, $R^3$, and $R^4$ are each independently hydrogen, hydroxy, $C_1$-$C_{12}$ alkyl, $C_1$-$C_{12}$ perhaloalkyl, $C_1$-$C_{12}$ alkoxy, $C_1$-$C_{12}$ perhaloalkoxy, $C_2$-$C_{12}$ alkenyl, $C_2$-$C_{12}$ alkynyl, ($C_1$-$C_6$ alkyl)-O-($C_1$-$C_6$ alkylene), or hydroxy ($C_1$-$C_6$ alkylene);
x and y are each independently an integer of 1 to 10;
z is an integer of 1 to 5;
$R^5$ is hydrogen or methyl;

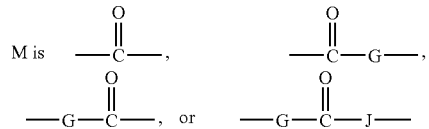

wherein G and J are each independently O or $NR^6$, wherein $R^6$ is hydrogen or $C_1$-$C_6$ alkyl;
m is 1, 2, 3, or 4;
W is an organic group having the valency of z+1; and
q is 0 or 1, and further wherein when a is 1, n+m+q is 1, 2, 3, or 4, and when a is 0, n+m+q is 1, 2, 3, 4, 5, or 6.

In another embodiment, a method of manufacturing a composition comprising a polymerizable (meth)acrylate comprises reacting a hydroxy-containing (meth)acrylate monomer of structure II:

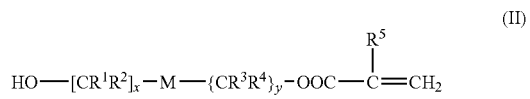

wherein
$R^1$, $R^2$, $R^3$, and $R^4$ are each independently hydrogen, hydroxy, $C_1$-$C_{12}$ alkyl, $C_1$-$C_{12}$ perhaloalkyl, $C_1$-$C_{12}$ alkoxy, $C_1$-$C_{12}$ perhaloalkoxy, $C_2$-$C_{12}$ alkenyl, $C_2$-$C_{12}$ alkynyl, ($C_1$-$C_6$ alkyl)-O—($C_1$-$C_6$ alkylene), or hydroxy ($C_1$-$C_6$ alkylene);
x and y are each independently an integer from 1 to 10;
$R^5$ is hydrogen or methyl; and M is

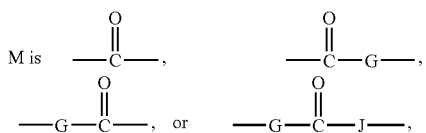

wherein G and J are each independently O or NR$^6$, wherein R$^6$ is hydrogen or C$_1$-C$_6$ alkyl, with an aromatic compound comprising anhydride functionality, carboxylic acid functionality, or a combination thereof In yet another embodiment, a method of making a dental restoration comprises applying to a site to be restored a composition comprising the above-described polymerizable (meth)acrylate of general structure I, and polymerizing the (meth)acrylate.

BRIEF DESCRIPTION OF THE FIGURE

The FIGURE is a graph illustrating cure time after ageing of a composition in accordance with the present invention and a control.

DETAILED DESCRIPTION OF PREFERRED EMBODIMENTS

The polymerizable (meth)acrylates described herein are useful as dental resins and possess improved properties over existing dental resins, and correspondingly enhance the properties of dental restorative materials prepared from such resins. For instance, the polymerizable (meth)acrylates provide excellent bonding strength between a dental substrate (dentin, enamel, or other tooth structure) and the dental restorative material made from the polymerizable (meth)acrylate. Additionally, dental restorative materials prepared from the polymerizable (meth)acrylates exhibit reduced shrinkage upon polymerization to provide a better seal between the dental restoration and the repaired tooth.

In particular, an improved dental resin is of formula I:

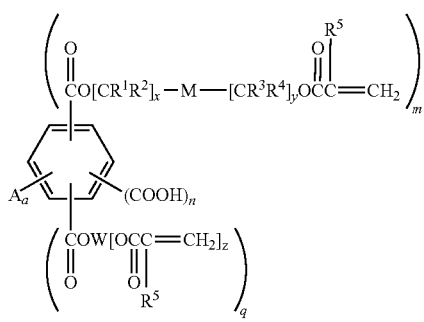

(I)

In structure I, n is 0, 1, 2, or 3, q is 0 or 1, A is an anhydride group, and a is 0 or 1. As is known, the anhydride group (—C(O)—O—C(O)—) is linked via its two carbon atoms to two ortho carbons of the phenyl ring. Preferably, a is 0. In another embodiment, a is 0 and n is preferably 1 or 2.

Further in structure I, R$^1$, R$^2$, R$^3$, and R$^4$ are each independently hydrogen, hydroxy, C$_1$-C$_{12}$ alkyl, C$_1$-C$_{12}$ perhaloalkyl, C$_1$-C$_{12}$ alkoxy, C$_1$-C$_{12}$ perhaloalkoxy, C$_2$-C$_{12}$ alkenyl, C$_2$-C$_{12}$ alkynyl, (C$_1$-C$_6$ alkyl)-O-(C$_1$-C$_6$ alkylene), or hydroxy(C$_1$-C$_6$ alkylene), wherein x and y are each independently an integer from 1 to 10. In one embodiment, R$^1$, R$^2$, R$^3$, and R$^4$ are each independently hydrogen, hydroxy, or C$_1$-C$_{12}$ alkyl, and x and y is each independently an integer from 1 to 6. More preferably R$^1$, R$^2$, R$^3$, and R$^4$ is each independently hydrogen or C$_1$-C$_6$ alkyl.

R$^5$ in structure I is a hydrogen or methyl group, and is preferably a methyl group.

M in structure I is a carbonyl-containing group, in particular

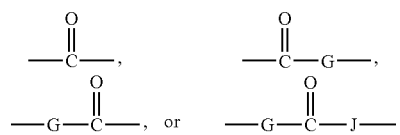

wherein G and J are each independently oxygen or NR$^6$, wherein R$^6$ is hydrogen or C$_1$-C$_6$ alkyl; and m is 1, 2, 3, or 4. Preferably, M is

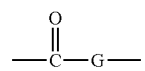

wherein G is oxygen, and m is 1, 2, or 3. When a is 1, n+m+q is 1, 2, 3, or 4, and when a is 0, n+m+is 1, 2, 3, 4, 5, or 6.

W in structure I is a hydrocarbyl linking group having a valency corresponding to z, the number of (meth)acrylate groups, plus one. W may be aromatic or aliphatic. Suitable aromatic groups are phenyl and napthyl, and suitable aliphatic groups are C$_1$-C$_{12}$ alkyl, cycloalkyl, alkenyl, or alkynyl groups.

Thus, in one embodiment, the improved dental resin composition comprises a polymerizable (meth)acrylate of the general structure III:

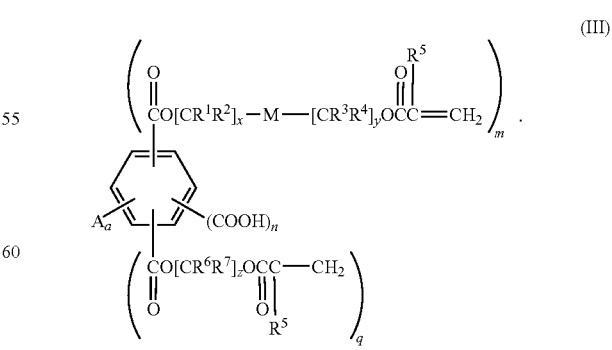

(III)

In structure III, n, q, M, A, and a are as described above. Preferably, a is 0 and n is 0 or 1.

Further in structure I, $R^1$, $R^2$, $R^3$, $R^4$, $R^5$, x, and y are as described above. $R^6$ and $R^7$ are each independently hydrogen, hydroxy, $C_1$-$C_{12}$ alkyl, $C_1$-$C_{12}$ perhaloalkyl, $C_1$-$C_{12}$ alkoxy, $C_1$-$C_{12}$ perhaloalkoxy, $C_2$-$C_{12}$ alkenyl, $C_2$-$C_{12}$ alkynyl, ($C_1$-$C_6$ alkyl)-O-($C_1$-$C_6$ alkylene), or hydroxy($C_1$-$C_6$ alkylene), wherein z is an integer of 1 to 5, preferably 1 to 3. In one embodiment, $R^1$, $R^2$, $R^3$, $R^4$, $R^6$, and $R^7$ are each independently hydrogen, hydroxy, or $C_1$-$C_{12}$ alkyl, and x and y is each independently an integer from 1 to 6. More preferably $R^1$, $R^2$, $R^3$, $R^4$, $R^6$, and $R^7$ is each independently hydrogen or $C_1$-$C_6$ alkyl.

The polymerizable (meth)acrylate (I) may be synthesized, for example, from the reaction of a hydroxy-containing (meth)acrylate monomer and an aromatic compound comprising anhydride or carboxylic acid functionality or their synthetic equivalents (e.g., a carboxylic acid halide, for example chloride). An exemplary synthetic preparation includes the reaction of one mole of an aromatic anhydride, for example benzenetetracarboxylic acid dianhydride (BTAD) or pyromellitic dianhydride (PMDA), with two moles of a hydroxy-containing (meth)acrylate, for example caprolactone 2-(methacryloyloxy)ethyl ester (CLMA, or 2-(6-hydroxy-1-oxo-hexyloxy)ethyl methacrylate), at elevated temperature in the presence of a catalyst, for example a catalytic amount of stannous ethylhexanoate (SEH). The resulting reaction product contains two (meth)acrylate groups and two carboxylic acid groups. Any number of the remaining carboxylic acid groups may further be reacted with an additional hydroxy-containing (meth)acrylate monomer to form a modified polymerizable (meth)acrylate. The ratio of moles of hydroxy-containing (meth)acrylate monomer to moles of anhydride or carboxylic acid, as well as the reaction conditions and/or starting materials, may be varied to provide a wide range of polymerizable (meth)acrylate products.

Exemplary aromatic compounds comprising anhydride functionality, carboxylic acid functionality, or a combination thereof useful to prepare the polymerizable (meth)acrylate of structure I include BTAD, PMDA, all isomers of benzenetetracarboxylic acid, preferably benzene-1,2,4,5-tetracarboxylic acid, 1,3-dihydro-1,3-dioxoisobenzofuran-4,5-dicarboxylic acid, 1,3-dihydro-1,3-dioxoisobenzofuran-5,6-dicarboxylic acid, trimellitic anhydride, trimellitic acid, terephthalic acid, phthalic acid, phthalic anhydride, benzoic acid, 4'-(4,4'-isopropylidenediphenoxy)-bis(phthalic anhydride) (IBA), and the like. Preferred aromatic anhydride and/or carboxylic acid compounds include BTAD, 1,3-dihydro-1,3-dioxoisobenzofuran-4,5-dicarboxylic acid, PMDA, benzene-1,2,4,5-tetracarboxylic acid, 1,3-dihydro-1,3-dioxoisobenzofuran-5,6-dicarboxylic acid, trimellitic anhydride, and trimellitic acid.

Suitable hydroxy-containing (meth)acrylate monomers include, for example, those of the general structure II:

(II)

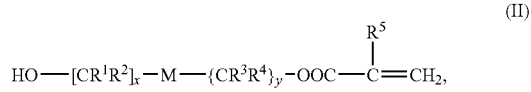

wherein $R^1$, $R^2$, $R^3$, $R^4$, x, y, and M are as described above.

A preferred hydroxy-containing (meth)acrylate monomer is a compound according to structure II wherein $R^1$, $R^2$, $R^3$, and $R^4$ are each hydrogen; x and y are each independently an integer from 1 to 5; M is

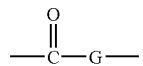

wherein G is oxygen; and $R^5$ is hydrogen or methyl, more preferably methyl. Non-limiting examples of suitable hydroxy-containing (meth)acrylate monomers according to structure II include CLMA, caprolactone 2-(acryloyloxy) ethyl ester, and 3-hydroxy-1-oxopropyl (meth)acrylate. The most preferred hydroxy-containing (meth)acrylate monomers are CLMA and caprolactone 2-(acryloyloxy)ethyl ester. Mixtures of two or more different hydroxy-containing (meth)acrylates of formula II may also be used.

Methods of synthesizing the hydroxy-containing (meth)acrylate monomers according to structure II can be found in the art. For example, CLMA may be prepared by the condensation of ε-caprolactone and 2-hydroxyethyl methacrylate. In yet another exemplary synthetic scheme, isocyanate alkyl (meth)acrylate (e.g., isocyanate methyl (meth)acrylate) may be reacted with a suitably monoprotected amino alcohol or dialcohol followed by deprotection to result in a hydroxy-containing methacrylate comprising urea or carbamate functionality.

When the polymerizable (meth)acrylate is prepared by the reaction of a hydroxy-containing (meth)acrylate monomer with an aromatic anhydride and/or carboxylic acid, the ratio of moles of hydroxy-containing (meth)acrylate monomer to the moles of aromatic anhydride, carboxylic acid, or its equivalent may be selected to obtain a resin that provides desired properties of adhesion and reduced shrinkage upon polymerization. The ratio of moles of hydroxy-containing (meth)acrylate monomer to moles of aromatic anhydride and/or carboxylic acid may be about 0.1 to about 5, preferably about 0.5 to about 4, more preferably about 0.75 to about 3, and yet more preferably about 1 to about 2.

The catalyst used to prepare the polymerizable (meth)acrylate according to the general structure (I) may be selected from metal organic catalysts comprising tin or titanium. Suitable non-limiting examples of tin-containing catalysts are dibutyltin dilaurate, dibutyltin maleate, dibutyltin diacetate, dioctyltin maleate, dibutyltin phthalate, stannous octoate, stannous naphthenate, stannous stearate, stannous 2-ethyl hexanoate, dibutyltin diacetylacetonate, dibutyltin oxide, and combinations comprising at least one of the foregoing tin based catalysts. Suitable non-limiting examples of titanium-based catalysts are tetrabutyl titanate, tetrapropyl titanate, tetraisopropyl titanate, triethanolamine titanate, titanium tetraacetylacetonate, and combinations comprising at least one of the foregoing titanium based catalysts. The preferred catalysts are stannous octoate or stannous 2-ethyl hexanoate.

It is generally desirable to use the catalyst in an amount of about 0.10 to about 10 mole percent based on the total moles of the reactant mixture. Within this range it is generally desirable to utilize the catalyst in an amount about 1 to about 8, preferably about 2 to about 7, and most preferably about 3 to about 6 mole percent based on the total moles of the reactants.

In another embodiment, the polymerizable (meth)acrylate of structure (I) may be formed by reaction of an aromatic compound comprising anhydride functionality, carboxylic acid functionality, or a combination thereof with a mixture comprising a hydroxy-containing (meth)acrylate of formula II and an additional, different hydroxy-containing methacrylate of formula IV:

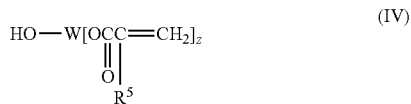

wherein W and $R^5$ are as defined above. Exemplary suitable hydroxy-containing (meth)acrylate monomers of this type include compounds comprising two or more (meth)acrylate groups, for example, glyceryl di(meth)acrylate, glycerol di(meth)acrylate, trimethylolpropane di(meth)acrylate; pentaerythritol tri(meth)acrylate and the like. Preferably, the different hydroxy-containing (meth)acrylate is of structure V:

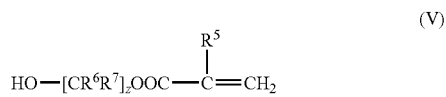

wherein $R^6$ and $R^7$ are each independently hydrogen, hydroxy, $C_1$-$C_{12}$ alkyl, $C_1$-$C_{12}$ perhaloalkyl, $C_1$-$C_{12}$ alkoxy, $C_1$-$C_{12}$ perhaloalkoxy, $C_2$-$C_{12}$ alkenyl, $C_2$-$C_{12}$ alkynyl, ($C_1$-$C_6$ alkyl)-O-($C_1$-$C_6$ alkylene), or hydroxy($C_1$-$C_6$ alkylene); z is an integer from 1 to 10; and $R^5$ is hydrogen or methyl. In a preferred embodiment, the additional hydroxy (meth)acrylate according to structure V comprises a compound wherein $R^6$ and $R^7$ are each independently hydrogen, $C_1$-$C_{12}$ alkyl, or hydroxy; and z is an integer from 1 to 10; and $R^5$ is methyl. Exemplary compounds include 2-hydroxyethyl methyacrylate (HEMA), 2-hydroxyethyl acrylate, hydroxypropyl (meth)acrylate, and glyceryl mono(meth)acrylate. Mixtures of the additional monomers may also be used.

When the polymerizable (meth)acrylate of structure I comprising free anhydride and/or carboxylic acid groups is reacted with an additional hydroxy-containing (meth)acrylate monomer, the ratio of the moles of additional hydroxy-containing (meth)acrylate monomer to moles of anhydride and/or carboxylic acid of structure I, monomer II, and the additional monomer(s) may be selected to provide a modified polymerizable (meth)acrylate possessing desired properties. Generally the ratio of moles of additional hydroxy-containing (meth)acrylate monomer to moles of anhydride and/or carboxylic acid groups of structure (I) may be about 0.1:1 to about 5:1, preferably about 0.5:1 to about 4:1, more preferably about 0.75:1 to about 3:1, and yet more preferably about 1:1 to about 2:1.

An exemplary polymerizable (meth)acrylate in accordance with the present invention is the reaction product of BTAD with CLMA, having structures VIa and/or VIb as follows:

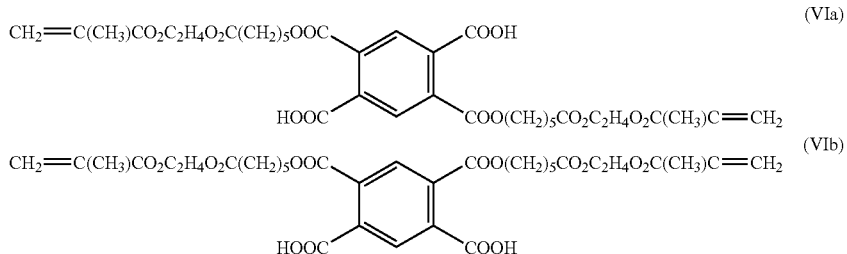

Another exemplary polymerizable (meth)acrylate in accordance with the present invention is the reaction product of BTAD with mixtures of CLMA and HEMA, having the structure (VIIa) and/or (VIIb) as follows:

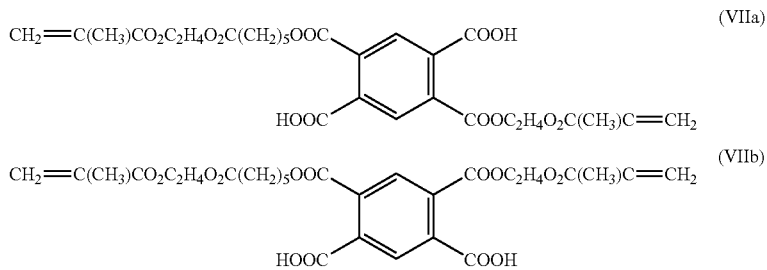

The polymerizable (meth)acrylates may be used alone or in combination with other co-polymerizable, ethylenically unsaturated monomers and/or oligomers. For example, one or more other co-polymerizable, ethylenically unsaturated monomers and/oligomers containing carboxylic acid(s), phosphoric acid(s), sulfonic acid(s) or their anhydride(s) may be utilized in combination with the polymerizable (meth) acrylates of this invention. Mixtures comprising the polymerizable (meth)acrylate and other components such as polymerization initiators, additives, and fillers may be prepared to form dental materials suitable for use as dental adhesives, dental cements, dental filling materials, root canal sealing/filling materials, and/or other dental restorative materials such as crown and bridge materials, provisional crown and bridge materials, and the like. It is generally desirable to use the polymerizable (meth)acrylate in an amount of about 1 to about 99 weight percent based on the total weight of the dental restorative material. Within this range it is generally desirable to use the polymerizable (meth)acrylate in an amount of about 10 to about 95 weight percent, preferably about 30 to about 90 weight percent, and most preferably about 50 to about 80 weight percent based on the total weight of the dental restorative material.

Known viscous resins may be used in combination with the polymerizable (meth)acrylate to provide a dental restorative material. Non-limiting examples include polyurethane dimethacrylates (PUDMA), diurethane dimethacrylates (DUDMA), and/or the polycarbonate dimethacrylate (PCDMA) disclosed in U.S. Pat. Nos. 5,276,068 and 5,444, 104 to Waknine, which is the condensation product of two parts of a hydroxyalkylmethacrylate and 1 part of a bis(chloroformate). Another advantageous resin having lower water sorption characteristics is an ethoxylated bisphenol A dimethacrylate (EBPDMA) as disclosed in U.S. Pat. No. 6,013,694 to Jia, et al. Still another useful resin material is disclosed in U.S. Pat. No. 6,787,629 to Jia, et al. An especially useful methacrylate resin is BisGMA.

Diluent monomers may be used to increase the surface wettability of the composition and/or to decrease the viscosity of the polymerization medium. Suitable diluent monomers include those known in the art such as hydroxyalkyl (meth)acrylates, for example 2-hydroxyethyl (meth)acrylate, 2-hydroxypropyl (meth)acrylate, and 4-hydroxybutyl (meth) acrylate; ethylene glycol (meth)acrylates, including ethylene glycol methacrylate, diethylene glycol methacrylate, tri(ethylene glycol) dimethacrylate and tetra(ethylene glycol) dimethacrylate; and diol dimethacrylates such as 1,4-butanediol di(meth)acrylate, dodecane diol di(meth)acrylate, or 1,6-hexanediol di(meth)acrylate, particularly 1,6-hexanediol dimethacrylate (HDDMA). Other suitable monomers include polyethylene glycol mono(meth)acrylate; glycerol di(meth) acrylate; trimethylolpropane di(meth)acrylate; pentaerythritol tri(meth)acrylate; the (meth)acrylate of phenyl glycidyl ether; and the like. Tri(ethylene glycol) dimethacrylate (TEGDMA) is particularly preferred.

Diluent monomers or viscous resins, when present, are incorporated into the dental restorative materials in an amount of about 1 to about 70 weight percent of the total dental restorative material.

The optional filler system may comprise one or more of the inorganic fillers currently used in dental composite materials. Preferred fillers include those, which are capable of being covalently bonded to the polymerizable (meth)acrylate matrix itself or to a coupling agent (e.g., silanes) that is covalently bonded to both. Examples of suitable filling materials include but are not limited to, silica, quartz, strontium silicate, strontium borosilicate, lithium silicate, lithium alumina silicate, amorphous silica, ammoniated or deammoniated calcium phosphate, tricalcium phosphate alumina, zirconia, tin oxide, titania and combinations comprising at least one of the foregoing fillers. Some of the aforementioned inorganic filling materials and methods of preparation thereof are known in the art, as disclosed in U.S. Pat. No. 4,544,359 and No. 4,547,531 to Waknine, pertinent portions of which are incorporated herein by reference. Organic-inorganic fillers of POSS™ (Hybrid Plastics) can be incorporated into the composites as disclosed in U.S. Patent Application Publication 2002/0198282 A1. Other organic-inorganic fillers such as zirconium methacrylate and zirconium dimethacrylate under the codes of CXZR050 and CXZR051 (Gelest, Inc.) can also be used. Suitable high refractive index filler materials such as high refractive index silica glass fillers; calcium silicate based fillers such as apatites, hydroxyapatites or modified hydroxyapatite compositions may also be used. Alternatively, inert, non-toxic radiopaque materials such as bismuth oxide ($Bi_2O_3$), bismuth oxychloride, zirconium oxide, barium sulfate, and bismuth subcarbonate in micro- or nano scaled sizes may be used. In addition, fibrous fillers such as those disclosed in U.S. Pat. Nos. 6,013,694, 6,403,676 and 6,270,562 to Jia and Jia et al. may also be used.

Suitable fillers have particle sizes of about 0.01 to about 5.0 micrometers, and may further comprise bound or unbound silicate colloids of about 0.001 to about 0.2 micrometers. These additional fillers may also be treated with a silane-coupling agent to increase adhesion with the polymerizable, (meth)acrylate. Commercially available silane treated fumed silica based on Aerosil A200 can be obtained from Degussa Corp under the names of Aerosil R711 and R7200.

The amount of total filler system in the dental restorative material can vary from about 1 to about 90 weight percent based on the total weight of the dental restorative material. The amount used is determined by the requirements of the particular application. Thus, for example, crown and bridge materials generally comprise about 60 to about 90 weight percent filler; luting cements comprise about 20 to about 80 weight percent filler; sealants generally comprise about 1 to about 20 weight percent filler; adhesives generally comprise about 1 to about 30 weight percent filler; and restorative materials comprise about 50 to about 90 weight percent filler, with the remainder in all cases being the polymerizable (meth)acrylate and other optionally added resins.

The polymerizable (meth)acrylate may be used together with a curing system, which generally includes polymerization initiators; polymerization accelerators; ultraviolet light absorbers; antioxidants; and other additives known in the art.

Suitable polymerization initiators are those initiators that can be utilized in UV-activated cure or visible light-activated cure compositions. For example, visible light-curable compositions employ light-sensitive compounds, including but not being limited to benzil, benzoin, benzoin methyl ether, DL-camphorquinone (CQ), and benzil diketones. Either UV-activated cure or visible light-activated cure (approximately 230 to 750 nanometer) is acceptable. The amount of photoinitiator is selected according to the curing rate desired. A minimal catalytically effective amount is generally about 0.01 weight percent of the total dental resin composition, and will lead to a slower cure. Faster rates of cure are achieved with amounts of catalyst in the range from greater than about 0.01 percent to about 5 weight percent of the total dental resin composition. The total dental resin composition is the total weight of the polymerizable (meth)acrylate and other resinous materials, such as for example, resinous diluents, which are used in the dental restorative material.

Alternatively, the dental restorative material may be formulated as a self-curing system. Self-curing dental composite materials will generally contain free radical polymerization initiators such as, for example, a peroxide in an amount of about 0.01 to about 1.0 weight percent of the total resin dental composite material. Particularly suitable free radical initiators are lauryl peroxide, tributyl hydroperoxide and, more particularly benzoyl peroxide (BPO).

Polymerization accelerators suitable for use are the various organic tertiary amines well known in the art. In visible light-curable dental restorative materials, the tertiary amines are generally (meth)acrylate derivatives such as dimethylaminoethyl methacrylate and, particularly, diethylaminoethyl methacrylate (DEAEMA) in an amount of about 0.05 to about 0.5 weight percent of the total dental restorative material. In the self-curing dental composite materials, the tertiary amines are generally aromatic tertiary amines, preferably tertiary aromatic amines such as ethyl 4-(dimethylamino)benzoate (EDMAB), 2-[4-(dimethylamino)phenyl]ethanol, N,N-dimethyl-p-toluidine (DMPT), and bis(hydroxyethyl)-p-toluidine (DHEPT). Such accelerators are generally present in an amount of about 0.5 to about 4.0 weight percent of the total dental restorative material.

It is furthermore preferred to employ an ultraviolet absorber in an amount of about 0.05 to about 5.0 weight percent of the total dental restorative material. Such UV absorbers are particularly desirable in the visible light-curable dental restorative materials in order to avoid discoloration of the resin from incident ultraviolet light. Suitable UV absorbers are the various benzophenones, particularly UV-5411 available from American Cyanamid Company.

In one embodiment, the polymerizable (meth)acrylate is prepared by reacting an aromatic compound comprising anhydride and/or carboxylic acid functionality with a hydroxy-containing (meth)acrylate monomer in the presence of a catalyst. The resulting polymerizable (meth)acrylate is then formulated into a dental restorative material by mixing with the filler system and the curing system. The dental restorative material is then applied to the tooth to be repaired, and cured.

Alternatively, the dental restorative material may be formulated as a two-part system, wherein the first part can comprise the polymerizable (meth)acrylate and the filler system. The second part can comprise the curing system and optional diluent monomers. When necessary, the two parts are metered out and then mixed using a spatula. The cure may be initiated through the use of UV light or by raising the temperature of the mixture. The dental restorative material thus obtained is then placed in the tooth to be restored after the tooth is appropriately prepared. Methods for use of the above-described compositions are well known in the art.

As used herein, the term "(meth)acrylate" is intended to encompass both acrylate and methacrylate groups. All ranges disclosed herein are inclusive and combinable. In addition, all patents are incorporated by reference in their entirety.

The invention is further illustrated by the following non-limiting examples.

EXAMPLE 1

Synthesis of BTAD-CLMA (Structure VI)

In a reaction flask, 1 mole (218 g) of 1,2,4,5-benzenetetracarboxylic dianhydride (BTAD) and 2.05 mole (500 g) of 2-(caprolactone)ethyl methacrylate (CLMA) were mixed and heated in an oil bath while mixing until the mixture becomes liquid. A catalytic amount of tin(II) 2-ethylhexanoate (SEH) was added into the flask slowly and the reaction monitored by Fourier transform infrared spectroscopy (FTIR). The reaction was stopped when the anhydride peak at 1782 $cm^{-1}$ disappeared. The final product BTAD-CLMA is a viscous liquid.

EXAMPLE 2

Synthesis of BTAD-CLMA-HEMA (Structure VII)

In a reaction flask, 1 mole (218 g) of 1,2,4,5-benzenetetracarboxylic dianhydride (BTAD), 1.05 mol (500 g) of 2-(caprolactone)ethyl methacrylate (CLMA) and 1 mol (130 g) 2-hydroxyethyl methacrylate (HEMA) was mixed. The mixture was heated in an oil bath while mixing until the mixture became liquid. A catalytic amount of tin(II) 2-ethylhexanoate (SEH) was added into the flask slowly and the reaction monitored by FTIR and stopped when the anhydride peak at 1782 $cm^{-1}$ disappeared. The final product BTAD-CLMA-HEMA is a viscous liquid.

EXAMPLE 3

Light-Curable Compositions Using the Synthesized Resins

The synthesized resins BTAD-CLMA and BTAD-CLMA-HEMA were each mixed with a conventional resin and diluent (PUDMA and HDDMA)in a weight ratio of 50/40/10. Quantities of 0.2 wt % CQ and 0.4 wt % EDMAB were added as photoinitiators. The samples were cured for a total four minutes using visible light with CureLite™ Plus curing box (Pentron Corp.) Samples were then trimmed and stored in water at 37° C. for 24 hours before testing.

Three point bending strength or flexural strength (MOR) was measured on all samples using an ATS machine as described in ISO 4049 for Resin Based Filling Materials (1997). Results are shown in Table 1, wherein standard deviations are in parentheses.

TABLE 1

| | BTAD-CLMA/ UDMA/HDDMA (Resin 1) | BTAD-CLMA-HEMA/ UDMA/HDDMA (Resin 2) |
| --- | --- | --- |
| MOR Mpa (σ) | 97(8) | 83(10) |

Resin 1 and Resin 2 were further used to make a light-curable dental composite with the addition of treated silica filler (R7200 from Degussa), a sol-gel processed zirconium silicate filler as disclosed in U.S. Patent Publ. No. 2003/0125444 A1 and Schott glass filler (Schott 8235, available from Schott Electronic Packaging Gmbh, Germany). The same filler combination and loading (78 wt. % filler) were used in to form Composite 1 from Resin 1 and Composite 2 from Resin 2. The composites were tested and the MOR results are shown in Table 2.

TABLE 2

| | Composite 1 | Composite 2 |
| --- | --- | --- |
| MOR Mpa (σ) | 149(12) | 124(17) |

EXAMPLE 4

Self-Curing Compositions Using the Synthesized Resins

Samples of self-curing compositions with and without BTAD-CLMA in the catalyst part were prepared to evaluate the effect BTAD-CLMA on cure. The samples, designated SC1 and SC2, were each formed from two paste components, a catalyst paste and a base paste. The catalyst past and base paste were each prepared from a resin and a filler that have the compositions shown in Table 3. The SC1 catalyst resin contains 10 wt. % of BTAD-CLMA, while SC2 does not. Other components for samples SC1 and SC2 are similar. In each sample, Catalyst paste 1 and Catalyst paste 2, respectively, were mixed in 1:1 wt. ratio with the base paste.

TABLE 3

| | SC1 | SC2 (Control) |
|---|---|---|
| Resin compositions used to form catalyst and base pastes | Catalyst resin 1: BPO 3 wt %, BHT 0.1 wt % in BisGMA/HDDMA/BTADCLMA (wt. Ratio: 60/30/10) Base resin: DHEPT 1.5 wt %, BHT 0.05 wt % in EBPADMA | Catalyst resin 2: BPO 3 wt %, BHT 0.1 wt % in BisGMA/HDDMA (wt. Ratio: 70/30) Base resin: DHEPT 1.5 wt %, BHT 0.05 wt % in EBPADMA |
| Paste Components | Catalyst paste 1: Catalyst resin 1: 35 wt % Filler: 65 wt % of treated silica and glass filler Base paste: Base resin: 30 wt % Filler: 70 wt % of treated silica and glass filler, barium sulfate and calcium hydroxide | Catalyst paste 2: Catalyst resin 2: 35 wt % Filler: 65 wt % of treated silica and glass filler Base paste: Base resin: 30 wt % Filler: 70 wt % of treated silica and glass filler, barium sulfate and calcium hydroxide |

Both samples were allowed to age, and portions of the samples were taken periodically to determine the gel times and setting times. The FIGURE shows the stability test results of samples SC1 and SC2 at room temperature for 8 weeks. Sample SC1 shows stable gel time and setting time during the 8 weeks storage at room temperature, but sample SC2 shows increasing gel time and setting time.

EXAMPLE 5

The present polymerizable (meth)acrylates resins can be used to prepare a light curable, one-component adhesive composite for tooth restorations, wherein the composites can be used without a separate dental bonding procedure prior to a the application of the material. Such procedures can be time-consuming, and their elimination is highly advantageous. An exemplary composition is illustrated in the table below:

| Components | Function in the composition | Parts per hundred |
|---|---|---|
| BTAD-CLMA-HEMA | Resin matrix component and adhesion promoter | 20 |
| HEMA | A co-polymerizable resin diluent and hydrophilicity modifier for the composition | 20 |
| Camphorquinone | Photo-initiator | 0.1 |
| Lucirin-TPO | Co-photo-initiator | 0.2 |
| BHT | stabilizer | 0.01 |
| Silane treated barium glass (Schott 8235) | filler | 55 |
| Amorphous silica (Degussa R 7200) | Filler and rheology/viscosity modifier | 4.69 |

The above composition has a flowable consistency, which allows delivery of the composite through a cannula, for example a needle tip directly onto a tooth surface. Again, it has been found that a separate bonding procedure, i.e. an additional bonding adhesive is not necessary. These compositions may be used, for example, for cementing a veneer, lining a tooth cavity underneath a regular dental restorative composite, sealing a root canal coronal end, placing as a direct tooth filling, securing an orthodontic bracket, or the like.

EXAMPLE 6

The present polymerizable (meth)acrylates resins can be used to prepare self and/or dual-curable two-component composites suitable for use as an adhesive luting cement, a core build-up material, a root canal filling/sealing material, or the like. In an advantageous feature, use of a separate bonding procedure before using the composite material is not necessary. An exemplary composition is illustrated in the table below.

| Components | Base Paste | Catalyst Paste |
|---|---|---|
| BTAD-CLMA | | 15 |
| 4-methacryloxyethyl trimellitic anhydride | | 15 |
| HEMA | 5 | 20 |
| UDMA | 35 | |
| BisGMA | 10 | |
| BHT | 0.01 | 0.1 |
| EDMAB | 0.5 | |
| Camphorquinone | 0.2 | |
| DHEPT | 1.0 | |
| BPO | | 2.0 |
| Silane treated barium glass filler (Schott 8235) | 30 | 5 |
| Al—Ca—F-silicate filler | 15 | |
| BiOCl | | 35 |
| Amorphous silica (OX-50) | 3.29 | 7.9 |

In self-cure mode, the working time and setting time of the above composition is about three minutes and four and half minutes, respectively, when the base and catalyst is mixed in 1:1 ratio by volume and the material is not subject to a second curing process. In dual-cure mode, when the material, upon mixing the base and catalyst, is subject to a dental visible light-curing source, the mass of the material will harden immediately upon the photoinitiation.

The Table below shows the results of cementation/bonding tests of the present polymerizable (meth)acrylates resin composite compositions between dentin and a ceramic (3G™ ceramic material, Pentron Corp., Wallingford, Conn.). The bonding test method was as follows:

1. 3G™ ceramic rods were fabricated with a dental porcelain furnace according to the ceramic firing temperature and conditions of the product. The 3G™ ceramic rods used for the bonding test have final dimensions of about 3.2 mm diameter and 6-8 mm length, on which one end of the rod was sandblasted, cleaned and then silane treated as per the product instructions. The treated end will be contacting the bonding cement as in a tooth restoration. Each test group contains 5 samples.

2. Teeth samples were prepared to expose the dentin and then the teeth were mounted with an acrylic material leaving the dentin exposed, which were then subject to sand paper grinding under wet condition to have a same surface pattern for all the test groups.

3. The cement materials were mixed according to the product instructions and applied onto the prepared, briefly dried tooth surface. The ceramic rod was then seated onto the cement surface under a 500 gram load with the aid of a BenCor Multi-test device (Danville Engineering, CA).

4. After the cement hardened, the bonded samples were transferred into a 100% humidity chamber held at 37° C. for 24 hours before the debond test.

5. The debond test was done in push shear mode using a BenCor testing device on an ATS testing machine. The load at which the bonded ceramic rod broke was recorded and the shear bonding strength of the testing sample was then calculated based on the rod surface area. Standard deviation is reported in parentheses.

| Cement Materials | Shear Bonding Strength (the stress needed to break the bond between the 3G ceramic and the tooth surface), MPa (S.D.) | Notes |
|---|---|---|
| Cement material as in Example 6 | 12.2 (2.8) | A paste-paste self-adhesive resin cement |
| Fleck's ® Zinc Cement (A conventional zinc phosphate cement for dental restorations) | 0.5 (0.8) | A powder-liquid cement system as a control available from Mizzy, Inc., Cherry Hill, NJ. |
| Lute-It! ™ resin cement, shade A2 | 0.3 (1.2) | A paste-paste conventional methacrylate resin cement as a control and used without a separated bonding procedure before the application of the cement available from Pentron Corp., Wallingford, CT. |
| Lute-It ™ resin cement, shade A2, used in conjunction with Bond-1 ™ dental adhesive | 14.8 (1.6) | Before apply the mixed cement onto the tooth surface, a separated bonding procedure is performed per the instruction of the Bond-1 ™ dental bonding system, available from Pentron Corp., Wallingford, CT. |

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended embodiments.

The invention claimed is:

1. A dental restorative composition comprising, based on total weight of the composition:

about 1 to about 99 weight percent of a polymerizable (meth)acrylate of the structure:

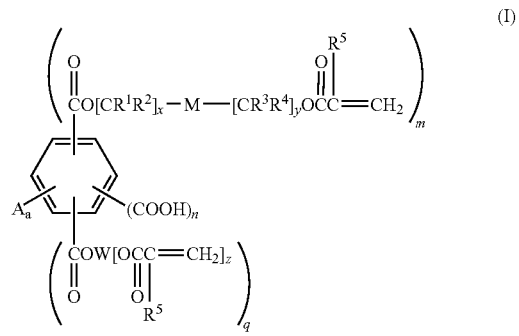

wherein

A is an anhydride;

a is 0 or 1;

n is 0, 1, 2, or 3;

$R^1$, $R^2$, $R^3$, and $R^4$ are each independently hydrogen, hydroxy, $C_1$-$C_{12}$ alkyl, $C_1$-$C_{12}$ perhaloalkyl, $C_1$-$C_{12}$ alkoxy, $C_1$-$C_{12}$ perhaloalkoxy, $C_2$-$C_{12}$ alkenyl, $C_2$-$C_{12}$ alkynyl, ($C_1$-$C_6$ alkyl)-O—($C_1$-$C_6$ alkylene), or hydroxy($C_1$-$C_6$ alkylene);

x and y are each independently an integer of 1 to 10; z is an integer of 1 to 5;

$R^5$ is hydrogen or methyl;

when q is 1, M is $$-\overset{O}{\underset{\|}{C}}-,\quad -\overset{O}{\underset{\|}{C}}-G-,$$

$$-G-\overset{O}{\underset{\|}{C}}-,\quad \text{or}\quad -G-\overset{O}{\underset{\|}{C}}-J-, \text{ and}$$

when q is 0, M is $$-\overset{O}{\underset{\|}{C}}-,\quad -\overset{O}{\underset{\|}{C}}-NR^6-,$$

$$-NR^6-\overset{O}{\underset{\|}{C}}-,\quad \text{or}\quad -G-\overset{O}{\underset{\|}{C}}-J-$$

wherein G and J are each independently O or $NR^6$, wherein $R^6$ is hydrogen or $C_1$-$C_6$ alkyl;

m is 1, 2, 3, or 4;

W is an organic group having the valency of z+1; and q is 0 or 1;

wherein $$\left(\overset{O}{\underset{\underset{|}{\|}}{C}}O[CR^1R^2]_x-M-[CR^3R^4]_yO\overset{OR_5}{\underset{\|}{C}}C=CH_2\right)_m$$

is different from $$\left(\underset{O}{\overset{|}{COW[O\underset{OR^5}{\overset{||}{CC}}=CH_2]_z}}\right)_{q;}$$

and further wherein when a is 1, n+m+q is 1, 2, 3, or 4, and when a is 0, n+m+q is 1, 2, 3, 4, 5, or 6;
about 1 to about 90 weight percent of a filler system; and
a curing system; wherein the dental restorative composition does not require a separate dental bonding procedure and has a shear bonding strength to a dentin surface of at least 12.2 MPa after curing.

2. The composition of claim 1, wherein $R^1$, $R^2$, $R^3$, and $R^4$ are each independently hydrogen or $C_1$-$C_{12}$ alkyl; and x and y are each independently an integer from 1 to 5.

3. The composition of claim 1, wherein a is 0; $R^1$, $R^2$, $R^3$, and $R^4$ are each independently hydrogen; x is 5; y is 2; and M is $$-\underset{O}{\overset{||}{C}}-G-,$$

wherein G is oxygen.

4. The composition of claim 3, wherein n is 0, 1, or 2.

5. The composition of claim 1, wherein the polymerizable (meth)acrylate has the structure:

$$\left(\underset{O}{\overset{O}{\overset{||}{CO[CR^1R^2]_x}}}-M-[CR^3R^4]_y\underset{O}{\overset{O}{\overset{||}{OCC}}}\underset{R^5}{\overset{R^5}{=}}CH_2\right)_m$$

$$A_a\overset{}{\underset{}{\bigcirc}}(COOH)_n$$

$$\left(\underset{O}{\overset{O}{\overset{||}{CO[CR^6R^7]_z}}}\underset{O}{\overset{O}{\overset{||}{OCC}}}\underset{R^5}{\overset{}{=}}CH_2\right)_q$$

wherein
$R^6$ and $R^7$ are each independently hydrogen, hydroxy, $C_1$-$C_{12}$ alkyl, $C_1$-$C_{12}$ perhaloalkyl, $C_1$-$C_{12}$ alkoxy, $C_1$-$C_{12}$ perhaloalkoxy, $C_2$-$C_{12}$ alkenyl, $C_2$-$C_{12}$ alkynyl, ($C_1$-$C_6$ alkyl)-O—($C_1$-$C_6$ alkylene), or hydroxy($C_1$-$C_6$ alkylene);
z is an integer of 1 to 5.

6. The composition of claim 5, wherein z is 1 to 3, $R^1$, $R^2$, $R^3$, $R^4$, $R^6$, and $R^7$ are each independently hydrogen, hydroxy, or $C_1$-$C_{12}$ alkyl, and x and y are each independently an integer from 1 to 6.

7. The composition of claim 1, wherein the polymerizable (meth)acrylate is prepared by the reaction of an aromatic compound comprising anhydride functionality, carboxylic acid functionality, or a combination thereof; and a first hydroxy-containing (meth)acrylate monomer of the structure:

$$HO-[CR^1R^2]_x-M-\{CR^3R^4\}_y-OOC-\underset{R^5}{\overset{R^5}{\overset{|}{C}}}=CH_2$$

wherein
$R^1$, $R^2$, $R^3$, and $R^4$ are each independently hydrogen, hydroxy, $C_1$-$C_{12}$ alkyl, $C_1C_{12}$ perhaloalkyl, $C_1$-$C_{12}$ alkoxy, $C_1$-$C_{12}$ perhaloalkoxy, $C_2$-$C_{12}$ alkenyl, $C_2$-$C_{12}$ alkynyl, ($C_1$-$C_6$ alkyl)-O—($C_1$-$C_6$ alkylene), or hydroxy ($C_1$-$C_6$ alkylene);
x and y are each independently an integer from 1 to 10;
$R^5$ is hydrogen or methyl; and when q is 1, M is $-\underset{O}{\overset{O}{\overset{||}{C}}}-$, $-\underset{O}{\overset{O}{\overset{||}{C}}}-G-$, $-G-\underset{O}{\overset{O}{\overset{||}{C}}}-$, or $-G-\underset{O}{\overset{O}{\overset{||}{C}}}-J-$, and when q is O, M is $-\underset{O}{\overset{O}{\overset{||}{C}}}-$, $-\underset{O}{\overset{O}{\overset{||}{C}}}-NR^6-$, $-NR^6-\underset{O}{\overset{O}{\overset{||}{C}}}-$, or $-G-\underset{O}{\overset{O}{\overset{||}{C}}}-J-$ wherein G and J are each independently O or $NR^6$, wherein $R^6$ is hydrogen or $C_1$-$C_6$ alkyl.

8. The composition of claim 7, wherein the aromatic compound is benzenetetracarboxylic acid; benzenetetracarboxylic acid dianhydride; 1,3-dihydro-1,3-dioxoisobenzofuran-4,5-dicarboxylic acid; pyromellitic dianhydride; benzene-1,2,4,5-tetracarboxylic acid; 1,3-dihydro-1,3-dioxoisobenzofuran-5,6-dicarboxylic acid; trimellitic anhydride; trimellitic acid; terephthalic acid; phthalic acid; phthalic anhydride; benzoic acid; or a combination comprising at least one of the foregoing aromatics.

9. The composition of claim 7, wherein the reaction further comprises an additional hydroxy-containing (meth)acrylate of the structure:

$$HO-W[O\underset{O}{\overset{||}{CC}}=CH_2]_z;$$
$$\underset{R^5}{|}$$

wherein
W is an organic group having the valency of z+1;
z is an integer of 1 to 5; and
$R^5$ is hydrogen or methyl,
wherein the additional hydroxy-containing (meth)acrylate is different than the first hydroxy-containing (meth)acrylate.

10. The composition of claim 9, wherein the additional hydroxy-containing (meth)acrylate has the structure:

$$HO-[CR^6R^7]_zOOC-\underset{}{\overset{R^5}{\overset{|}{C}}}=CH_2$$

wherein $R^6$ and $R^7$ are each independently hydrogen, hydroxy, $C_1$-$C_{12}$ alkyl, $C_1$-$C_{12}$ perhaloalkyl, $C_1$-$C_{12}$ alkoxy, $C_1$-$C_{12}$ perhaloalkoxy, $C_2$-$C_{12}$ alkenyl, $C_2$-$C_{12}$ alkynyl, ($C_1$-$C_6$alkyl)-O—($C_1$-$C_6$ alkylene), or hydroxy($C_1$-$C_6$ alkylene); z is an integer from 1 to 10; and $R^5$ is hydrogen or methyl.

11. The composition of claim 1, further comprising an additional ethylenically unsaturated monomer and/or oligomer that is co-curable with the polymerizable (meth)acrylate.

12. A method of manufacturing a dental restorative composition, comprising:
mixing, based on total weight of the dental restorative composition,
about 1 to about 99 weight percent of a polymerizable (meth)acrylate of the structure:

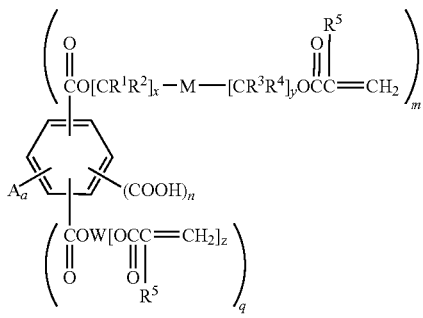

(I)

wherein
A is an anhydride;
a is 0 or 1;
n is 0, 1, 2, or 3;
$R^1$, $R^2$, $R^3$, $R^4$ each independently hydrogen, hydroxy, $C_1$-$C_{12}$ alkyl, $C_1$-$C_{12}$ perhaloalkyl, $C_1$-$C_{12}$ alkoxy, $C_1$-$C_{12}$ perhaloalkoxy, $C_2$-$C_{12}$ alkenyl, $C_2$-$C_{12}$ alkynyl, ($C_1$-$C_6$ alkyl)-O—($C_1$-$C_6$ alkylene), or hydroxy ($C_1$-$C_6$ alkylene);
x and y are each independently an integer of 1 to 10;
z is an integer of 1 to 5;
$R^5$ is hydrogen or methyl;

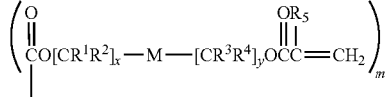

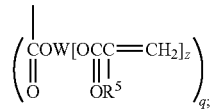

wherein G and J are each independently O or $NR^6$, wherein $R^6$ is hydrogen or $C_1$-$C_6$ alkyl;
m is 1, 2, 3, or 4;
W is an organic group having the valency of z+1; and
q is 0 or 1;
wherein

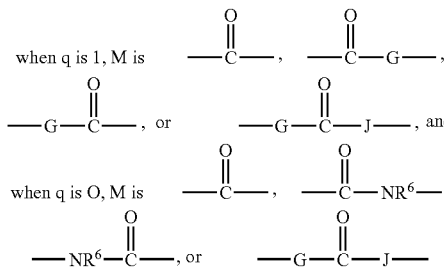

is different from and further wherein when a is 1, n+m+q is 1, 2, 3, or 4, and when a is 0, n+m+q is 1, 2, 3, 4, 5, or 6;
about 1 to about 90 weight percent of a filler system; and a curing system; wherein
the dental restorative composition does not require a separate dental bonding procedure and has a shear bonding strength to a dentin surface of at least 12.2 MPa after curing.

13. A method of repairing a tooth, comprising preparing the tooth;

applying a dental restorative composition to a tooth, the dental restorative composition comprising, based on the total weight of the composition:
about 1 to about 99 weight percent of a polymerizable (meth)acrylate of the structure:

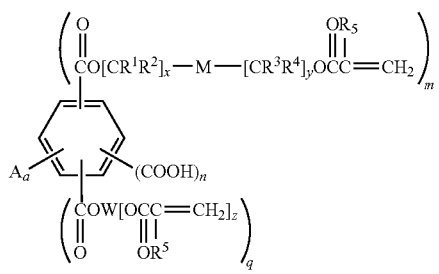

(I)

wherein
A is an anhydride:
a is 0 or 1;
n is 0, 1, 2, or 3;
$R^1$, $R^2$, $R^3$, and $R^4$ are each independently hydrogen hydroxy, $C_1$-$C_{12}$ alkyl, $C_1$-$C_{12}$ perhaloalkyl, $C_1$-$C_{12}$ alkoxy, $C_1$-$C_{12}$ perhaloalkoxy, $C_2$-$C_{12}$ alkenyl, $C_2$-$C_{12}$ alkynyl ($C_1$-$C_6$ alkyl)-O—($C_1$-$C_6$ alkylene), or hydroxy($C_1$-$C_6$ alkylene);
x and y are each independently an integer of 1 to 10; z is an integer of 1 to 5;
$R^5$ is hydrogen or methyl;

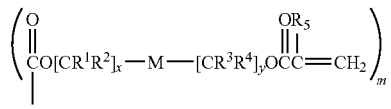

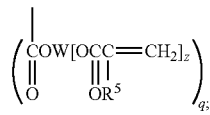

wherein G and J are each independently O or $NR^6$, wherein $R^6$ is hydrogen or $C_1$-$C_6$ alkyl;
m is 1, 2, 3, or 4;
w is an organic group having the valency of z+1; and
q is 0 or 1;
wherein

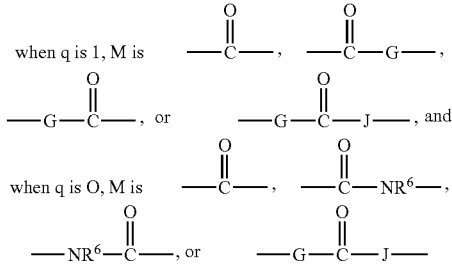

is different from and further wherein a is 1, n+m+q is 1, 2, 3, or 4, and when a is 0, n+m+q is 1, 2, 3, 4, 5, or 6;
about 1 to about 90 weight percent of a filler system; a curing system; and curing the dental restorative composition; wherein the dental restorative composition does not require a separate dental bonding procedure and has a shear bonding strength to a dentin surface of at least 12.2 MPa after curing.

* * * * *